US008242277B2

(12) United States Patent
Cantrell et al.

(10) Patent No.: US 8,242,277 B2
(45) Date of Patent: Aug. 14, 2012

(54) PREPARATION OF TETRAHYDROISOQUINOLINES FROM DIHYDROISOQUINOLINES

(75) Inventors: Gary L. Cantrell, Troy, IL (US); Dan P. Magparangalan, Gainesville, FL (US); Frank W. Moser, Arnold, MO (US); Jian Bao, Chesterfield, MO (US); Christopher W. Grote, Webster Groves, MO (US); Peter X. Wang, Chesterfield, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 440 days.

(21) Appl. No.: 12/518,430

(22) PCT Filed: Dec. 10, 2007

(86) PCT No.: PCT/US2007/025262
§ 371 (c)(1),
(2), (4) Date: Jun. 10, 2009

(87) PCT Pub. No.: WO2008/073389
PCT Pub. Date: Jun. 19, 2008

(65) Prior Publication Data
US 2010/0022776 A1    Jan. 28, 2010

Related U.S. Application Data

(60) Provisional application No. 60/874,456, filed on Dec. 12, 2006.

(51) Int. Cl.
*C07D 217/02* (2006.01)
(52) U.S. Cl. ...................................... 546/149
(58) Field of Classification Search .......... None
See application file for complete search history.

(56) References Cited

U.S. PATENT DOCUMENTS

| | | | |
|---|---|---|---|
| 4,521,601 A | 6/1985 | Rice | |
| 4,991,391 A | 2/1991 | Kosinski | |
| 6,887,999 B1 | 5/2005 | Likhotvorik | |

FOREIGN PATENT DOCUMENTS

| | | |
|---|---|---|
| CN | 1115318 | 1/1996 |
| CN | 1115318 A | 1/1996 |
| DE | 922 827 | 1/1955 |
| WO | 2006/052430 | 5/2006 |

OTHER PUBLICATIONS

Huang et al., "Synthesis of (+−)-Glaucine and (+−)-Neospirodienone via an One-Pot Bischler-Napieralski Reaction and Oxidative Coupling by a Hypervalent Iodine Reagent", Helvetica chimica Acta 2004 CH, vol. 887, No. 1, 2004, pp. 167-174, XP002476119.
Venkov et al., "Synthesis of isoquinolines from 2-phenylethylamines, amides, nitriles and carboxylic acids in polyphosphoric acid", Tetrahedron 19960909 GB, vol. 52, No. 37, Sep. 9, 1996, pp. 12299-12308, XP 002476120.
Beyerman et al., "Synthesis of racemic and optically active codeine and morphine via the N-formylnordihydrothebainones", Journal of the Royal Netherlands Chemical Society, 97, May 5, 1978, pp. 127-130.
Beyerman et al., "Synthesis of racemic and of ( + )- and ( − )-1 methyldihydrothebainone. (Chemistry of opium alkaloids, Part IV)", Recl. Trav. Chim. Pays-Bas, 1976, 75, p. 184-188.
Farber et al., "A Synthesis of Armepavine and Related Bases. Resolution of (±)-Armepavine", Anales. Asoc. Quim. Argentina, 58, 1970, pp. 133-138.
Farber et al., "Resolution of (±)-armepavine", Chemistry and Industry, Jan. 13, 1968, pp. 57-58.
Kametani et al., "131. Coclaurine 7-Benzyloxy-1,2,3,4-tetrahydro-1-(p-hydroxyphenyl)-6-methoxy-2-methylisoquinoline 7-Benzyloxy-1,2,3,4-tetrahydro-1-(p-hydroxybenzyl)-6-methoxy-2-methylisoquinoline", Coclaurine, vol. 87, No. 7, 1967, pp. 757-760.
Kashdan et al., "Synthesis of 1,2,3,4-Tetrahydroisoquinolines", J. Org. Chem., 1982, 47, pp. 2638-2643.
Kitamura et al., "General Asymmetric Synthesis of Isoquinoline Alkaloids. Enantioselective Hydrogenation of Enamides Catalyzed by BINAP-Ruthenium(II) Complexes", J. Org. Chem., 1994, 59, pp. 297-310.
Meuzelaar et al., "Chemistry of Opium Alkaloids, 45 Improvements in the Total Synthesis of Morphine", Eur. J. Org. Chem., 1999, pp. 2315-2321.
Nagata et al., "Synthetic Studies on Isoquinoline Alkaloids. I. An Efficient Synthesis of 9,10-Substituted Protoberberine Alkaloids", Chem. Pharm. Bull., 194, 23(11), pp. 2867-2877, 1975.
Saunders et al., "Assessment of relative nutritive value of proteins using streptoccus zymogenes", Chemistry and Industry, Jan. 13, 1968, pp. 56-58.
Sheth et al., "Synthesis of N-(3',4'-Dimethoxy-5'-bromophenethyl)-2-(4"-hydrioxyphenyl)- acetamide & Allied Products", Indian Journal of Chemistry, vol. 15B, Jul. 1977, pp. 595-598.
Small et al., "The Addition of Organomagnesium Halides to Pseudocodeine Types. IV. Nuclear-Substituted Morphine Derivatives", Contribution from the Cobb Chemical Laboratory, University of Virginia, Received Jun. 6, 1938, pp. 204-232.
Uematsu et al., "Asymmetric Transfer Hydrogenation of Imines", J. Am. Chem. Soc., 1996, 118, pp. 4916-4917.
H.C. van der Plas et al., "On the reaction of 2-, 3- and 4-bromo(chloro)-1,8-naphthyridine with potassium amide in liquid ammonia", Laboratory of Organic Chemistry, Agricultural University, Wagenagen, The Netherlands, (Received Oct. 10, 1977).
Lespagnol et al., "Préparation d'amides de l'homovératrylamine et d'acides iodophénylacétiques substitués", Chim. Therap., 1965, 1, pp. 14-16.
Lespagnol et al., "Preparation of amides from the homoveratrylamine and iodephenylacetic substituted acids", Chim. Therap., 1965, pp. 14-16, English Translation by FAST-TRANS.

(Continued)

*Primary Examiner* — Zinna Northington Davis

(57) ABSTRACT

The present invention is directed to processes for the synthesis of morphinans. In particular, a process for the asymmetric reduction of an imine moiety in a 3,4-dihydroisoquinoline to produce a tetrahydroisoquinoline, followed by a Birch reduction to produce a hexahydroisoquinoline. In various embodiments, the 3,4-dihydroisoquinoline contains a phenol moiety protected with a labile protecting group. In other embodiments, the imine reduction reaction mixture contains silver tetrafluoroborate.

17 Claims, No Drawings

OTHER PUBLICATIONS

Tolkachev et al., " ", Organicheskoi Khimii, 1966, 36(10), pp. 1767-1772.

Tolkachev et al., "Synthetic Investigation in [Kurarealkaloidov] Area XVI. Synthesis 1-(e'-Bromine . . . ", Organicheskoi Khimii, 1966, 36(10), pp. 1767-1772, English Translation proviced by FAST-TRANS.

Voronin et al., "Synthetic Investigations in the Field of the Curare Alkaloids XII. Synthesis of Isomeric Tubocurarin Iodides", Chemistry of heterocyclic Compounds, Chemistry of Heterocyclic Compounds, 1967, pp. 447-450 (English Translation of Voronin et al., Khimiya Geterotsiklicheskikh Soedinenii, 1969, 4, pp. 606-610).

Greene et al., "Protection for Phenols", Protective Groups in Organic Synthesis, $3^{rd}$, Ed., c1999, pp. 249-257 and 266-269.

Klunenberg et al., "A Remarkable Influence of the Electrolyte in Andoic cyclization of 1-Benzyltetrahydroisoquinolines to neospirodienones or Morphinandienones", Tetrahedron Letters, 1982, vol. 23, No. 44, pp. 4581-4584.

Rice, K.C. "Synthetic opium alkaloids and derivatives. A short total synthesis of (+-)-dihydrothebainone, (+-)-dihydrocodeinone, and (+-)-nordihydrocodeinone as an approach to a practical synthesis of morphine, codeine, and congeners"; Journal of Organic Chemistry, American Chemical Society, Easton; (1980); pp. 3135-3137; vol. 45, No. 15.

Passarella D. et al; "A convenient synthesis of [Delta]<7,8>-Morphinan-6-one and its direct oxidation to 14-hydroxy-[Delta]<7,8>-morphinan-6-one"; Bioorganic and Medicinal Chemistry Letters; (2002); pp. 1981-1983; vol. 12, No. 15.

Database Beilistein(Online); Beilstein Institute for Organic Chemistry, Frankfurt-Main, DE; 1967.

Database Beilstein (Online); Beilstein Institute for Organic Chemistry, Frankfurt-Main., DE, 1966.

Database Beilstein (Online): Beilstein Institute for Organic Chemistry, Frankfurt-Main, DE, 1975.

EP patent application No. 0901065.0 extended search report.

PREPARATION OF TETRAHYDROISOQUINOLINES FROM DIHYDROISOQUINOLINES

CROSS REFERENCE TO RELATED APPLICATIONS

This application is a national stage application of PCT/US2007/025262, filed Dec. 10, 2007, which claims the benefit of U.S. Provisional Application No. 60/874,456 filed Dec. 12, 2006.

FIELD OF THE INVENTION

The present invention generally relates to processes for the synthesis of intermediates used to prepare morphinans. More specifically, the invention is directed to the synthesis of hexahydroisoquinolines and their analogs from dihydroisoquinolines.

BACKGROUND OF THE INVENTION

Hexahydroisoquinoline and its derivatives are important synthetic intermediates to many morphinan compounds including burprenorphine, codeine, etorphine, hydrocodone, hydromorphone, morphine, nalbuphine, nalmefene, naloxone, naltrexone, oxycodone, and oxymorphone. Generally, these compounds are analgesics, which are used extensively for pain relief in the field of medicine due to their action as opiate receptor agonists. However, nalmefene, naloxone and naltrexone are opiate receptor antagonists; they are used for reversal of narcotic/respiratory depression due to opiate receptor agonists.

Rice (U.S. Pat. No. 4,521,601) discloses the reduction of a dihydroisoquinoline to a tetrahydroisoquinoline by contacting the dihydroisoquinoline with sodium cyanoborohydride or sodium borohydride in refluxing 45% methanol for 1.5 hours. Rice further discloses Birch reduction of a tetrahydroisoquinoline to a hexahydroisoquinoline with lithium or sodium in liquid ammonia at −55° C. to −65° C. for 4 hours, then at −75° C. until none of the starting tetrahydroisoquinoline remains by thin layer chromatography. Because the borohydride reduction of a dihydroisoquinoline occurs in an achiral environment, the resulting tetrahydroisoquinoline must be resolved before further reaction. This resolution adds an extra step and reduces the yield of the desired enantiomer as half of the product has the undesired stereochemistry.

Uematsu et al. (*J. Am. Chem. Soc.* 1996, 113, 4916-4917) and Meuzelaar, et al. (*Eur. J. Org. Chem.* 1999, 2315-2321) disclose the asymmetric reduction of a dihydroisoquinoline with a chiral ruthenium catalyst in the presence of a 5:2 formic acid-triethylamine azeotropic mixture of salts in various aprotic solvents. These transformations typically have a reaction time of about 3 hours. Thus, more efficient processes having higher yields and enantiomeric excesses are desirable.

SUMMARY OF THE INVENTION

Among the various aspects of the invention is a process for the preparation of a 1,2,3,4-tetrahydroisoquinoline corresponding to Formula 700 comprising treating a 3,4-dihydroisoquinoline corresponding to Formula 600 with an asymmetric catalyst in the presence of silver tetrafluoroborate, and a hydrogen source. The chemical structures corresponding to Formulae 600 and 700 are

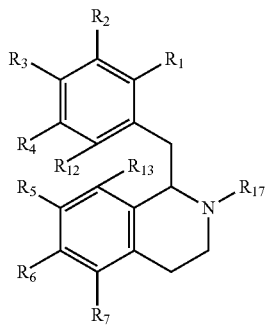

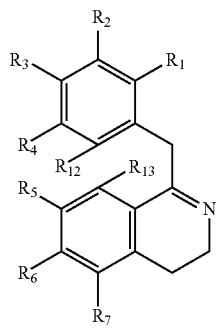

wherein $R_1$ and $R_7$ are independently hydrogen, hydrocarbyl, substituted hydrocarbyl, or $-OR_{111}$; $R_2$ is hydrogen, hydrocarbyl, substituted hydrocarbyl, halo, or $-OR_{211}$; $R_3$ is hydrogen, hydrocarbyl, substituted hydrocarbyl, or $-OR_{311}$; $R_4$ is hydrogen, hydrocarbyl, substituted hydrocarbyl, halo, or $-OR_{411}$; $R_5$ and $R_6$ are independently hydrogen, hydrocarbyl, substituted hydrocarbyl, or $-OR_{511}$; $R_{12}$ is hydrogen, hydrocarbyl, substituted hydrocarbyl, halo, or $-OR_{121}$; $R_{13}$ is hydrogen, hydrocarbyl, substituted hydrocarbyl, or $-OR_{511}$; $R_{17}$ is hydrogen, or acyl; $R_{111}$ is hydrogen, hydrocarbyl, or substituted hydrocarbyl; $R_{211}$ is hydrogen, hydrocarbyl, $-C(O)R_{212}$, $-C(O)NHR_{213}$, or $-SO_2R_{214}$; $R_{212}$, $R_{213}$, and $R_{214}$ are independently hydrocarbyl or substituted hydrocarbyl; $R_{311}$ is hydrogen, hydrocarbyl, $-C(O)R_{312}$, $-C(O)NHR_{313}$, or $-SO_2R_{314}$; $R_{312}$, $R_{313}$, and $R_{314}$ are independently hydrocarbyl or substituted hydrocarbyl; $R_{411}$ is hydrogen, hydrocarbyl, $-C(O)R_{412}$, $-C(O)NHR_{413}$, or $-SO_2R_{414}$; $R_{412}$, $R_{413}$, and $R_{414}$ are independently hydrocarbyl or substituted hydrocarbyl; $R_{511}$ is hydrogen, hydrocarbyl, or substituted hydrocarbyl; and $R_{121}$ is hydrogen, hydrocarbyl, or substituted hydrocarbyl.

Another aspect is a process for the preparation of a tetrahydroisoquinoline corresponding to Formula 701 comprising treating a 3,4-dihydroisoquinoline corresponding to Formula 601 with an asymmetric catalyst in the presence of a hydrogen source. The chemical structures corresponding to Formulae 601 and 701 are

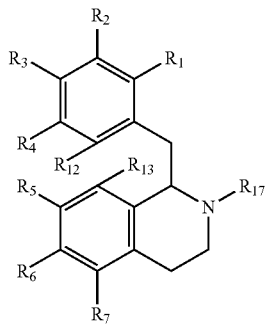

-continued

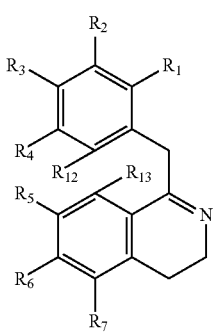

601 wherein $R_1$, $R_2$, $R_3$, $R_4$, $R_5$, $R_6$, $R_7$, $R_{12}$, $R_{13}$, $R_{17}$, $R_{111}$, $R_{211}$, $R_{212}$, $R_{213}$, $R_{214}$, $R_{311}$, $R_{312}$, $R_{313}$, $R_{314}$, $R_{411}$, $R_{413}$, $R_{414}$, $R_{511}$, and $R_{121}$ are as defined above in connection with Formulae 600 and 700; $R_{412}$ is alkyl or aryl, provided, $R_{412}$ is other than methyl; and wherein at least one of $R_2$, $R_3$, or $R_4$ is —OC(O)$R_{212}$, —OC(O)NHR$_{213}$, —OSO$_2$R$_{214}$, —OC(O)R$_{312}$, —OC(O)NHR$_{313}$, —OSO$_2$R$_{314}$, —OC(O)R$_{412}$, —OC(O)NHR$_{413}$, or —OSO$_2$R$_{414}$.

Yet another aspect is a process for the preparation of a hexahydroisoquinoline corresponding to Formula 800 comprising reducing a tetrahydroisoquinoline corresponding to Formula 704

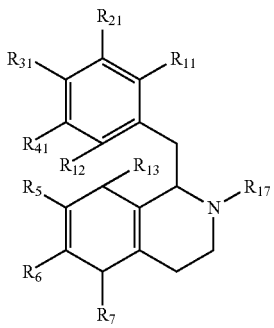

800

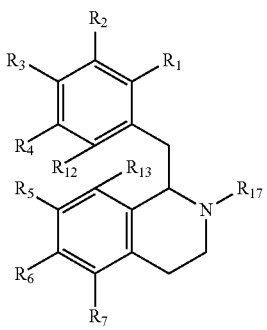

704 wherein $R_1$, $R_2$, $R_3$, $R_4$, $R_5$, $R_6$, $R_7$, $R_{12}$, $R_{13}$, $R_{17}$, $R_{111}$, $R_{211}$, $R_{212}$, $R_{213}$, $R_{214}$, $R_{311}$, $R_{312}$, $R_{313}$, $R_{314}$, $R_{411}$, $R_{413}$, $R_{414}$, $R_{511}$, and $R_{121}$ are as defined above in connection with Formulae 600 and 700; $R_{21}$ is hydrogen, hydrocarbyl, substituted hydrocarbyl, halo, or —OR$_{215}$; $R_{31}$ is hydrogen, hydrocarbyl, substituted hydrocarbyl, or —OR$_{315}$; $R_{41}$ is hydrogen, hydrocarbyl, substituted hydrocarbyl, halo, or —OR$_{415}$; $R_{215}$ is hydrogen, hydrocarbyl or substituted hydrocarbyl; $R_{315}$ is hydrogen, hydrocarbyl or substituted hydrocarbyl; $R_{412}$ is hydrogen, alkyl or aryl, provided, $R_{412}$ is other than phenyl; $R_{415}$ is hydrogen, hydrocarbyl or substituted hydrocarbyl; and wherein either $R_1$ is hydroxyl, and/or at least one of $R_2$, $R_3$, or $R_4$ is hydroxyl, —OC(O)$R_{212}$, —OC(O)NHR$_{213}$, —OSO$_2$R$_{214}$, -OC(O)R$_{312}$, —OC(O)NHR$_{313}$, —OSO$_2$R$_{314}$, —OC(O)R$_{412}$, —OC(O)NHR$_{413}$, or —OSO$_2$R$_{414}$.

A further aspect of the invention is a compound corresponding to Formula 703

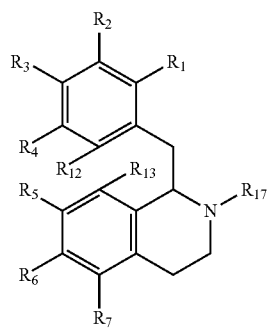

703 wherein $R_1$, $R_2$, $R_3$, $R_4$, $R_5$, $R_6$, $R_7$, $R_{12}$, $R_{13}$, $R_{17}$, $R_{111}$, $R_{211}$, $R_{213}$, $R_{212}$, $R_{214}$, $R_{311}$, $R_{312}$, $R_{313}$, $R_{314}$, $R_{411}$, $R_{413}$, $R_{414}$, $R_{511}$, and $R_{121}$ are as defined above in connection with Formulae 600 and 700; $R_{412}$ is alkyl or aryl, provided, $R_{412}$ is other than methyl or phenyl; and wherein at least one of $R_2$, $R_3$, or $R_4$ is —OC(O)$R_{212}$, —OC(O)NHR$_{213}$, —OSO$_2$R$_{214}$, —OC(O)R$_{312}$, —OC(O)NHR$_{313}$, —OSO$_2$R$_{314}$, —OC(O)R$_{412}$, —OC(O)NHR$_{413}$, or —OSO$_2$R$_{414}$.

Other objects and features will be in part apparent and in part pointed out hereinafter.

DETAILED DESCRIPTION OF THE INVENTION

The present invention is directed to an improved synthetic method for preparing optically active hexahydroisoquinolines. Among the various aspects of the present invention is the preparation of various hexahydroisoquinolines (Formula 800) from the stepwise reduction of particular dihydroisoquinolines (Formulae 600 and 601). For example, in some of the various embodiments, a dihydroisoquinoline is reduced in the presence of a hydrogen source, an asymmetric catalyst, and, optionally, silver tetrafluoroborate to produce an optically active tetrahydroisoquinoline (Formulae 700, 701, and 702). The optically active tetrahydroisoquinoline can subsequently undergo a Birch reduction by contact with a reducing agent to form a hexahydroisoquinoline (Formula 800) without loss of optical activity. Various dihydroisoquinolines (Formula 601) and tetrahydroisoquinolines (Formulae 701 and 702) of the invention are substituted with ester, amide, or sulfonate ester protecting groups in order to facilitate reaction and isolation of intermediates.

Generally, the processes for the synthetic transformations of the invention described above are depicted in Reaction Scheme 1 below.

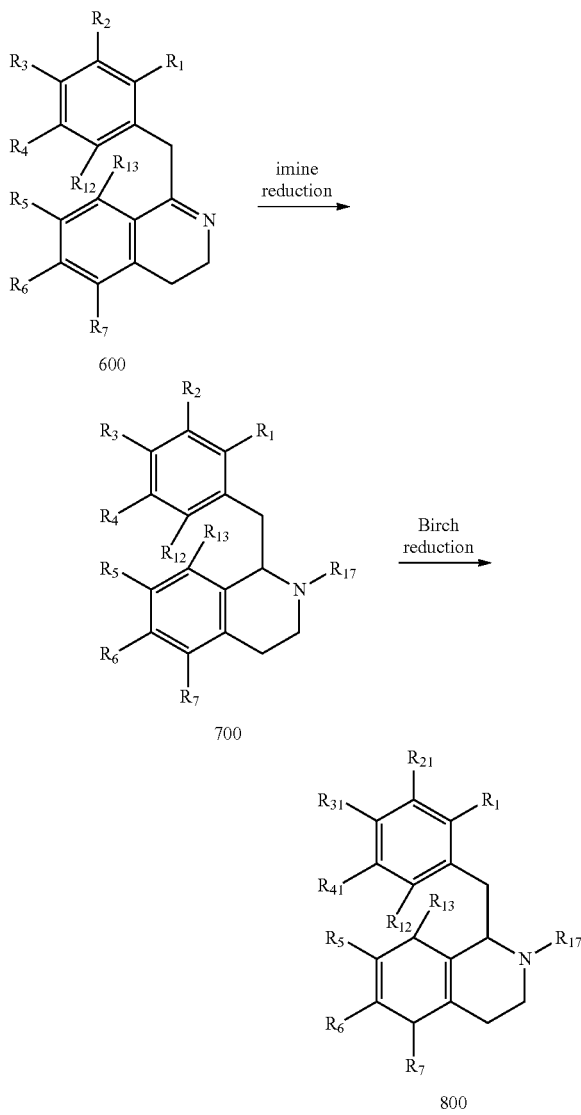

Reaction Scheme 1

600

700

800

Each of these compounds and synthetic steps are described in more detail below.

Hexahydroisoquinolines

As described above for Reaction Scheme 1, an aspect of the present invention is a process for preparing hexahydroisoquinolines corresponding to Formula 800

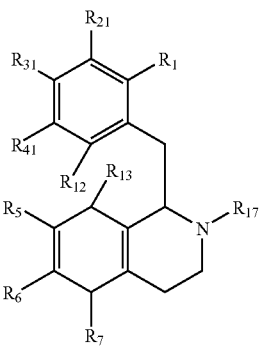

800 wherein $R_1$ is hydrogen, hydrocarbyl, substituted hydrocarbyl, or —$OR_{111}$;

$R_5$, $R_6$, $R_7$, and $R_{13}$ are independently hydrogen, hydrocarbyl, substituted hydrocarbyl, or —$OR_{512}$;

$R_{12}$ is hydrogen, hydrocarbyl, substituted hydrocarbyl, halo, or —$OR_{121}$;

$R_{17}$ is hydrogen or acyl;

$R_{21}$ is hydrogen, hydrocarbyl, substituted hydrocarbyl, halo, or —$OR_{215}$;

$R_{31}$ is hydrogen, hydrocarbyl, substituted hydrocarbyl, or —$OR_{315}$;

$R_{41}$ is hydrogen, hydrocarbyl, substituted hydrocarbyl, halo, or —$OR_{415}$;

$R_{111}$ is hydrogen, hydrocarbyl, or substituted hydrocarbyl;
$R_{121}$ is hydrogen, hydrocarbyl, or substituted hydrocarbyl;
$R_{215}$ is hydrogen, hydrocarbyl or substituted hydrocarbyl;
$R_{315}$ is hydrogen, hydrocarbyl or substituted hydrocarbyl;
$R_{415}$ is hydrogen, hydrocarbyl or substituted hydrocarbyl;
$R_{512}$ is hydrocarbyl, or substituted hydrocarbyl; and wherein at least one of $R_1$, $R_{21}$, $R_{31}$, or $R_{41}$ is hydroxyl.

Although $R_{21}$ is hydrogen, hydrocarbyl, substituted hydrocarbyl, halo, or —$OR_{215}$, in some of the various embodiments, $R_{21}$ is hydrogen or —$OR_{215}$. In some of these embodiments, $R_{215}$ is hydrogen, alkyl, or aryl. Preferably, $R_{215}$ is hydrogen or alkyl. More preferably, $R_{215}$ is hydrogen, methyl, ethyl, propyl, butyl, pentyl, hexyl, or phenyl. In some of the various embodiments, $R_{215}$ is hydrogen, methyl, or phenyl.

Similarly, although $R_{31}$ is hydrogen, hydrocarbyl, substituted hydrocarbyl, or —$OR_{315}$, in some embodiments, $R_{31}$ is hydrogen or —$OR_{315}$. In some of these embodiments, $R_{315}$ is hydrogen, alkyl, or aryl. Preferably, $R_{315}$ is hydrogen or alkyl. More preferably, $R_{315}$ is hydrogen, methyl, ethyl, propyl, butyl, pentyl, hexyl, or phenyl. In some of the various embodiments, $R_{315}$ is hydrogen, methyl, or phenyl.

As noted above, $R_{41}$ is hydrogen, hydrocarbyl, substituted hydrocarbyl, halo, or —$OR_{415}$, in some embodiments, $R_{41}$ is hydrogen or —$OR_{415}$. In some of these embodiments, $R_{415}$ is hydrogen, alkyl or aryl. More preferably, $R_{415}$ is hydrogen, methyl, ethyl, propyl, butyl, pentyl, hexyl, or phenyl. In some of the various embodiments, $R_{415}$ is hydrogen, methyl, or phenyl.

Further, $R_6$ is hydrogen, hydrocarbyl, substituted hydrocarbyl, or —$OR_{511}$, in some embodiments, $R_6$ is hydrogen or —$OR_{511}$. In some of these embodiments, $R_{511}$ is hydrogen, alkyl, or aryl. Preferably, $R_{511}$ is hydrogen, methyl, ethyl, propyl, butyl, pentyl, hexyl, or phenyl; more preferably, methyl.

As noted above, $R_{12}$ is hydrogen, hydrocarbyl, substituted hydrocarbyl, halo, or —$OR_{121}$, in some embodiments, $R_{12}$ is hydrogen, alkyl, alkenyl, aryl, aralkyl, or halo. Preferably, $R_{12}$ is hydrogen, alkyl, allyl, benzyl, or halo.

In many of the various embodiments, $R_1$, $R_5$, $R_7$, and $R_{13}$ are hydrogen.

In combination, among the preferred embodiments are hexahydroisoquinolines corresponding to Formula 800 wherein $R_{21}$ is hydrogen or —$OR_{215}$ wherein $R_{215}$ is hydrogen, alkyl, or aryl. In some embodiments, $R_{215}$ is hydrogen or methyl. In these embodiments, $R_{31}$ is hydrogen or —$OR_{315}$. In various preferred embodiments, $R_{315}$ is hydrogen, alkyl, or aryl, preferably, $R_{315}$ is hydrogen or alkyl. In some of these embodiments, $R_{315}$ is hydrogen or methyl. Further, $R_{41}$ is hydrogen or —$OR_{415}$. In various embodiments, $R_{415}$ is hydrogen, alkyl, or aryl, preferably, $R_{415}$ is hydrogen or alkyl. In some embodiments, $R_{415}$ is hydrogen or methyl. Further yet, $R_6$ is hydrogen or —$OR_{511}$. In some of these embodiments, $R_{511}$ is hydrogen, methyl, ethyl, propyl, butyl, pentyl, hexyl, or phenyl; preferably, hydrogen or methyl. Additionally, $R_{12}$ is hydrogen, alkyl, allyl, benzyl, or halo. In many of these embodiments, $R_1$, $R_5$, $R_7$, and $R_{13}$ are hydrogen.

Tetrahydroisoquinolines

As described in Reaction Scheme 1, a tetrahydroisoquinoline corresponding to Formula 700 has the structure

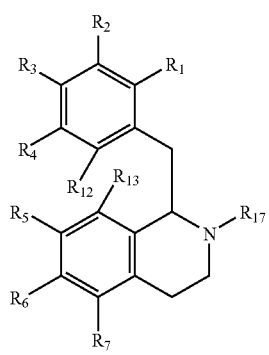

wherein $R_1$ and $R_7$ are independently hydrogen, hydrocarbyl, substituted hydrocarbyl, or —$OR_{111}$;

$R_2$ is hydrogen, hydrocarbyl, substituted hydrocarbyl, halo, or —$OR_{211}$;

$R_3$ is hydrogen, hydrocarbyl, substituted hydrocarbyl, or —$OR_{311}$;

$R_4$ is hydrogen, hydrocarbyl, substituted hydrocarbyl, halo, or —$OR_{411}$;

$R_5$ and $R_6$ are independently hydrogen, hydrocarbyl, substituted hydrocarbyl, or —$OR_{511}$;

$R_{12}$ is hydrogen, hydrocarbyl, substituted hydrocarbyl, halo, or —$OR_{121}$;

$R_{13}$ is hydrogen, hydrocarbyl, substituted hydrocarbyl, halo, or —$OR_{511}$;

$R_{17}$ is hydrogen or acyl;

$R_{111}$ is hydrogen, hydrocarbyl, or substituted hydrocarbyl;

$R_{211}$ is hydrogen, hydrocarbyl, —$C(O)R_{212}$, —$C(O)NHR_{213}$, or —$SO_2R_{214}$;

$R_{212}$, $R_{213}$, and $R_{214}$ are independently hydrocarbyl or substituted hydrocarbyl;

$R_{311}$ is hydrogen, hydrocarbyl, —$C(O)R_{312}$, —$C(O)NHR_{313}$, or —$SO_2R_{314}$;

$R_{312}$, $R_{313}$, and $R_{314}$ are independently hydrocarbyl or substituted hydrocarbyl;

$R_{411}$ is hydrogen, hydrocarbyl, —$C(O)R_{412}$, —$C(O)NHR_{413}$, or —$SO_2R_{414}$;

$R_{412}$, $R_{413}$, and $R_{414}$ are independently hydrocarbyl or substituted hydrocarbyl;

$R_{511}$ is hydrogen, hydrocarbyl, or substituted hydrocarbyl;

$R_{121}$ is hydrogen, hydrocarbyl, or substituted hydrocarbyl; and wherein at least one of $R_1$, $R_2$, $R_3$, or $R_4$ is hydroxyl, or at least one of $R_2$, $R_3$, or $R_4$ is —$OC(O)R_{212}$, —$OC(O)NHR_{213}$, or —$OSO_2R_{214}$.

In various embodiments, the tetrahydroisoquinoline structure corresponds to Formula 701 wherein $R_1$, $R_2$, $R_3$, $R_4$, $R_5$, $R_6$, $R_7$, $R_{12}$, $R_{13}$, $R_{111}$, $R_{211}$, $R_{213}$, $R_{214}$, $R_{311}$, $R_{312}$, $R_{313}$, $R_{314}$, $R_{411}$, $R_{412}$, $R_{413}$, $R_{414}$, $R_{511}$, and $R_{121}$ are defined as above for Formula 700; wherein at least one of $R_2$, $R_3$, or $R_4$ is —$OC(O)R_{212}$, —$OC(O)NHR_{213}$, —$OSO_2R_{214}$, —$OC(O)R_{312}$, —$OC(O)NHR_{313}$, —$OSO_2R_{314}$, —$OC(O)R_{412}$, —$OC(O)NHR_{413}$, or —$OSO_2R_{414}$; and $R_{412}$ is alkyl or aryl, provided, $R_{412}$ is other than methyl.

In some embodiments, the tetrahydroisoquinoline structure corresponds to Formula 702 wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{312}$, $R_{313}$, $R_{314}$, $R_{411}$, $R_{413}$, $R_{414}$, $R_{511}$, and $R_{121}$ are defined as above for Formula 700; wherein at least one of $R_2$, $R_3$, or $R_4$ is —$OC(O)R_{212}$, —$OC(O)NHR_{213}$, —$OSO_2R_{214}$, —$OC(O)R_{312}$, —$OC(O)NHR_{313}$, —$OSO_2R_{314}$, —$OC(O)R_{412}$, —$OC(O)NHR_{413}$, or —$OSO_2R_{414}$; and $R_{412}$ is alkyl or aryl, provided, $R_{412}$ is other than phenyl.

In other embodiments, the tetrahydroisoquinoline structure corresponds to Formula 703 wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{312}$, $R_{313}$, $R_{314}$, $R_{411}$, $R_{413}$, $R_{414}$, $R_{511}$, and $R_{121}$ are defined as above for Formula 700; wherein at least one of $R_2$, $R_3$, or $R_4$ is —$OC(O)R_{212}$, —$OC(O)NHR_{213}$, —$OSO_2R_{214}$, —$OC(O)R_{312}$, —$OC(O)NHR_{313}$, —$OSO_2R_{314}$, —$OC(O)R_{412}$, —$OC(O)NHR_{413}$, or —$OSO_2R_{414}$; and $R_{412}$ is alkyl or aryl, provided, $R_{412}$ is other than methyl or phenyl.

In some of the embodiments, the tetrahydroisoquinoline structure corresponds to Formula 704 wherein $R_1$, $R_{21}$, $R_{31}$, $R_{41}$, $R_5$, $R_6$, $R_7$, $R_{12}$, $R_{13}$, $R_{111}$, $R_{211}$, $R_{213}$, $R_{214}$, $R_{311}$, $R_{312}$, $R_{313}$, $R_{314}$, $R_{411}$, $R_{412}$, $R_{413}$, $R_{414}$, $R_{512}$, and $R_{121}$ are defined as above for Formula 800 and wherein at least one of $R_1$, $R_{21}$, $R_{31}$, or $R_{41}$ is hydroxyl.

Although $R_2$ is hydrogen, hydrocarbyl, substituted hydrocarbyl, halo, or —$OR_{211}$, in some of the various embodiments, $R_2$ is hydrogen or —$OR_{211}$. In some of these embodiments, $R_{211}$ is hydrogen, alkyl, aryl, —$C(O)R_{212}$, —$C(O)NHR_{213}$, or —$SO_2R_{214}$. Preferably, $R_{211}$ is hydrogen, alkyl, or —$C(O)R_{212}$ wherein $R_{212}$ is alkyl or aryl. More preferably, $R_{211}$ is —$C(O)R_{212}$ wherein $R_{212}$ is methyl, ethyl, propyl, butyl, pentyl, hexyl, or phenyl. In some of the various embodiments, $R_{211}$ is —$C(O)R_{212}$ wherein $R_{212}$ is ethyl, propyl, butyl, pentyl, or hexyl.

Similarly, although $R_3$ is hydrogen, hydrocarbyl, substituted hydrocarbyl, or —$OR_{311}$, in some embodiments, $R_3$ is hydrogen or —$OR_{311}$. In some of these embodiments, $R_{311}$ is hydrogen, alkyl, aryl, —$C(O)R_{312}$, —$C(O)NHR_{313}$, or —$SO_2R_{314}$. Preferably, $R_{311}$ is hydrogen, alkyl, or —$C(O)R_{312}$ wherein $R_{312}$ is alkyl or aryl. More preferably, $R_{311}$ is —$C(O)R_{312}$ wherein $R_{312}$ is methyl, ethyl, propyl, butyl, pentyl, hexyl, or phenyl. In some of the various embodiments, $R_{311}$ is —$C(O)R_{312}$ wherein $R_{312}$ is ethyl, propyl, butyl, pentyl, or hexyl.

As noted above, $R_4$ is hydrogen, hydrocarbyl, substituted hydrocarbyl, halo, or —$OR_{411}$, in some embodiments, $R_4$ is hydrogen or —$OR_{411}$. In some of these embodiments, $R_{411}$ is hydrogen, alkyl, aryl, —$C(O)R_{412}$, —$C(O)NHR_{413}$, or —$SO_2R_{414}$. Preferably, $R_{411}$ is hydrogen, alkyl, or —$C(O)R_{412}$ wherein $R_{412}$ is alkyl or aryl. More preferably, $R_{411}$ is —$C(O)R_{412}$ wherein $R_{412}$ is ethyl, propyl, butyl, pentyl, or hexyl.

Further, $R_6$ is hydrogen, hydrocarbyl, substituted hydrocarbyl, or —$OR_{511}$, in some embodiments, $R_6$ is hydrogen or —$OR_{511}$. In some of these embodiments, $R_{511}$ is hydrogen, alkyl, or aryl. Preferably, $R_{511}$ is hydrogen, methyl, ethyl, propyl, butyl, pentyl, hexyl, or phenyl; more preferably, methyl.

As noted above, $R_{12}$ is hydrogen, hydrocarbyl, substituted hydrocarbyl, halo, or —$OR_{121}$, in some embodiments, $R_{12}$ is hydrogen, alkyl, alkenyl, aryl, aralkyl, or halo. Preferably, $R_{12}$ is hydrogen, alkyl, allyl, benzyl, or halo.

In many of the various embodiments, $R_1$, $R_5$, $R_7$, and $R_{13}$ are hydrogen.

In combination, among the preferred embodiments are tetrahydroisoquinolines corresponding to Formulae 700, 701, 702, and 703 wherein $R_2$ is hydrogen or $—OR_{211}$ wherein $R_{211}$ is hydrogen, alkyl, or $—C(O)R_{212}$ wherein $R_{212}$ is alkyl or aryl. In some embodiments, $R_{212}$ is ethyl, propyl, butyl, pentyl, or hexyl. In these embodiments, $R_3$ is hydrogen or $—OR_{311}$. In various preferred embodiments, $R_{311}$ is hydrogen, alkyl, aryl, or $—C(O)R_{312}$, preferably, $R_{311}$ is hydrogen, alkyl, or $—C(O)R_{312}$ wherein $R_{312}$ is alkyl or aryl. In some of these embodiments, $R_{312}$ is ethyl, propyl, butyl, pentyl, or hexyl. Further, $R_4$ is hydrogen or $—OR_{411}$. In various embodiments, $R_{411}$ is hydrogen, alkyl, aryl, or $—C(O)R_{412}$, preferably, $R_{411}$ is hydrogen, alkyl, or $—C(O)R_{412}$ wherein $R_{412}$ is alkyl or aryl. In some embodiments, $R_{412}$ is methyl, ethyl, propyl, butyl, pentyl, hexyl, or phenyl. Alternatively, $R_{412}$ is ethyl, propyl, butyl, pentyl, or hexyl. Further yet, $R_6$ is hydrogen or $—OR_{511}$. In some of these embodiments, $R_{511}$ is hydrogen, methyl, ethyl, propyl, butyl, pentyl, hexyl, or phenyl; preferably, methyl. Additionally, $R_{12}$ is hydrogen, alkyl, allyl, benzyl, or halo. In many of these embodiments, $R_1$, $R_5$, $R_7$, and $R_{13}$ are hydrogen.

Dihydroisoquinolines

As described above for Reaction Scheme 1, a 3,4-dihydroisoquinoline corresponding to Formula 600 has the structure

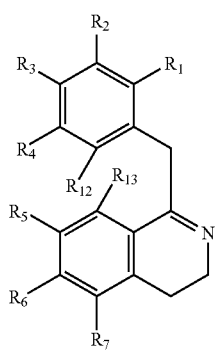

600 wherein $R_1$, $R_2$, $R_3$, $R_4$, $R_5$, $R_6$, $R_7$, $R_{12}$, and $R_{13}$ are defined as above in connection with Formula 700.

In various embodiments, the dihydroisoquinoline structure corresponds to Formula 601 wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{312}$, $R_{313}$, $R_{314}$, $R_{411}$, $R_{413}$, $R_{414}$, $R_{511}$, and $R_{121}$ are defined as above for Formula 600; wherein at least one of $R_2$, $R_3$, or $R_4$ is $—OC(O)R_{212}$, $—OC(O)NHR_{213}$, $—OSO_2R_{214}$, $—OC(O)R_{312}$, $—OC(O)NHR_{313}$, $—OSO_2R_{314}$, $—OC(O)R_{412}$, $—OC(O)NHR_{413}$, or $—OSO_2R_{414}$; and $R_{412}$ is alkyl or aryl, provided, $R_{412}$ is other than methyl.

Preferred substituent groups and preferred combinations of substituent groups for $R_1$, $R_2$, $R_3$, $R_4$, $R_5$, $R_6$, $R_7$, $R_{12}$, and $R_{13}$ are detailed above in connection with Formula 700.

Generally, compounds of Formulae 600 and 601 can be prepared by methods described by Rice in U.S. Pat. No. 4,521,601, herein incorporated by reference. Further, these compounds can be prepared by methods described by Kashdan et al. (J. Org. Chem. 1982, 47 2638-2643) and by Beyerman et al. (J. Royal Netherlands Chem. Soc. 1978, 97(5), 127-130), and by copending application U.S. Application Ser. No. 60/874,131, herein incorporated by reference.

Asymmetric Reduction of a 3,4-Dihydroisoquinoline to a Tetrahydroisoquinoline

For the process of the present invention, the structures of the products (e.g., hexahydroisoquinolines), reactants (e.g., 3,4-dihydroisoquinolines) and intermediates (e.g., tetrahydroisoquinolines) are described above. The first step of this process comprises a reduction of the imine moiety in a 3,4-dihydroisoquinoline to produce a tetrahydroisoquinoline. This imine reduction reaction mixture typically contains the 3,4-dihydroisoquinoline, the asymmetric catalyst, and a hydrogen source. The imine reduction reaction mixture can optionally contain silver tetrafluoroborate.

This imine reduction reaction forms another chiral center in the tetrahydroisoquinoline, and thus, preferably, occurs in an asymmetric environment. In various embodiments, the process of the invention uses an asymmetric catalyst to provide an asymmetric environment for the reduction of the imine moiety. The asymmetric catalyst comprises a metal or metal source and a chiral ligand. The metal or metal source is selected from ruthenium, a ruthenium complex, osmium, an osmium complex, rhodium, a rhodium complex, iridium, iridium complex, and combinations thereof. The chiral ligand can have the structure of formulae 670 or 680

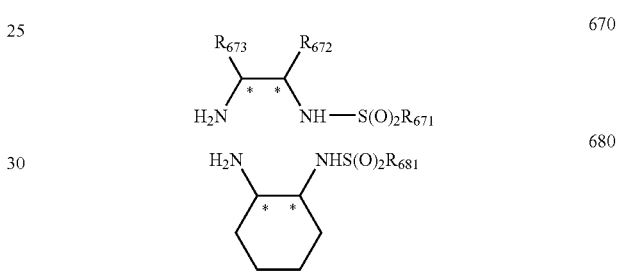

wherein $R_{671}$, $R_{672}$, and $R_{673}$ are independently alkyl or aryl and wherein $R_{681}$ is alkyl or aryl.

In various preferred embodiments, the chiral ligand can have the structure of 670 wherein $R_{672}$ and $R_{673}$ are phenyl and $R_{671}$ is aryl. In some of these embodiments, $R_{671}$ can be tolyl, mesityl, or naphthyl. In various preferred embodiments, the chiral ligand can be (1S,2S)-(+)-N-4-toluenesulfonyl-1,2-diphenylethylene-1,2-diamine or (1R,2R)-(−)-N-4-toluenesulfonyl-1,2-diphenylethylene-1,2-diamine, depending on which enantiomer is the desired product. In other embodiments, the chiral ligand can have the structure of 680 wherein $R_{681}$ is tolyl, mesityl, 2,4,6-triisopropylphenyl, or naphthyl. In particular embodiments, $R_{681}$ can be p-tolyl, 2,4,6-triisopropylphenyl, 1-naphthyl, or 2-naphthyl.

In various preferred embodiments, the asymmetric catalyst comprises a ruthenium source comprising dichloro(p-cymene) ruthenium (II) dimer and a chiral ligand comprising (1S,2S)-(+)-N-4-toluenesulfonyl-1,2-diphenylethylene-1,2-diamine. Typically, about 0.005 g to about 0.015 g of asymmetric catalyst per gram of starting 3,4-dihydroisoquinoline is present in the imine reduction reaction mixture.

The rate of the imine reduction reaction is directly proportional to the concentration of asymmetric catalyst (e.g., metal or metal source and chiral ligand) used. For example, an imine reduction reaction mixture that contains a greater amount of asymmetric catalyst has a shorter reaction time than a reaction mixture that contains a smaller amount of asymmetric catalyst.

In some of the embodiments, the hydrogen source for the imine reduction comprises protic compounds (including alcohol and formic acid). Preferably, the hydrogen source is a protic compound comprising a carboxylic acid. Particularly, the hydrogen source comprises a formic acid-triethylamine azeotropic mixture of salts; preferably, this mixture has a ratio of formic acid to triethyl amine of about 5:2. About 3 equivalents to about 3.5 equivalents of triethylamine and about 7.5 equivalents to about 8 equivalents of formic acid are used for each equivalent of 3,4-dihydroisoquinoline.

In various preferred embodiments, the reaction mixture can contain silver tetrafluoroborate. Typically, the silver tetrafluoroborate is present in similar amounts as the asymmetric catalyst and typically, ranges from about 0.005 g to about 0.015 g of silver tetrafluoroborate per gram of starting 3,4-dihydroisoquinoline present in the imine reduction reaction mixture. The addition of silver tetrafluoroborate increases the reaction rate. For example, the reaction time for the reduction in the presence of silver tetrafluoroborate is about 30% to about 50% shorter than the reaction time for the reduction in the absence of silver tetrafluoroborate.

Upon addition of the formic acid and triethylamine to the reaction mixture, there is an exotherm; this exotherm is followed by cooling of the reaction mixture and addition of the 3,4-dihydroisoquinoline and the asymmetric catalyst. The imine reduction occurs at a temperature of from about 10° C. to about 40° C.; preferably, from about 20° C. to about 30° C.; more preferably, from about 24° C. to about 26° C. The imine reduction reaction mixture is allowed to react for about 4 hours to about 24 hours; preferably for about 18 hours.

The imine reduction reaction mixture typically includes an aprotic, polar solvent. This solvent can be selected from acetonitrile, dimethylsulfoxide (DMSO), tetrahydrofuran (THF), halocarbons (e.g., dichloromethane, chloroform), dimethylformamide (DMF), dimethylacetamide (DMAC), N-methyl pyrrolidinone (NMP), and combinations thereof. Preferably, the solvent comprises acetonitrile.

Upon completion of the imine reduction, the product tetrahydroisoquinoline precipitates from the solution and can be isolated by methods known in the art. For example, the product can be collected by filtration of the reaction mixture followed by washing the product solid with the solvent.

Birch Reduction of a Tetrahydroisoquinoline to a Hexahydroisoquinoline

The second step of the process of the invention is a Birch reduction of a tetrahydroisoquinoline (Formulae 700, 701, 702, and 703) to form a hexahydroisoquinoline (Formula 800). The Birch reduction is generally effected using a reducing agent. Thus, the Birch reduction reaction mixture comprises a tetrahydroisoquinoline and a reducing agent. Exemplary reducing agents comprise an alkali metal and at least one of liquid ammonia, methylamine, ethylamine, ethylenediamine, and combinations thereof. Preferably, the reducing agent for the Birch reduction comprises lithium metal and liquid ammonia. In alternative embodiments, the reducing agent comprises lithium metal, sodium metal, potassium metal, or calcium metal and methylamine or ethylamine.

The Birch reduction reaction mixture typically also includes a solvent mixture. This solvent mixture comprises isopropyl alcohol (IPA), t-butyl alcohol, tetrahydrofuran (THF), ammonia, and combinations thereof. Preferably, the solvent comprises IPA, THF, and ammonia; and, in some embodiments, the ratio of IPA to THF to liquid ammonia is 1 to 2 to 3. Depending on the reagents used, the Birch reduction occurs at a temperature of from about −80° C. to about 10° C. When liquid ammonia is used as a reagent, the reduction takes place at about −80° C. to about −35° C. When methylamine or ethylamine is used as a reagent, the reduction takes place at a temperature from about −10° C. to about 10° C. The Birch reduction reaction mixture is maintained at the above temperatures for about 10 minutes to about 4 hours.

Typically, the tetrahydroisoquinoline was suspended or dissolved in a cosolvent such as tetrahydrofuran or t-butyl alcohol. This mixture was cooled to −10° C. and methylamine was added and the temperature was maintained at −10° C. The lithium metal was charged in portions and the reaction mixture was stirred at −10° C. for another 30 minutes to about 2 hours after sufficient lithium metal was charged. The reaction mixture was warmed to room temperature and then added to water to produce the product hexahydroisoquinoline as a precipitate.

Uses of Intermediates

The above-described synthesis stages are important in the preparation of morphinans and analogs thereof. General reaction schemes for the preparation of morphinans are disclosed in U.S. Pat. No. 4,368,326 to Rice, the entire disclosure of which is incorporated by reference. The morphinans and analogs thereof (i.e., the morphinans contain an X group of N—($R_{17}$) or N$^+$—($R_{17a}R_{17b}$)) of interest in the practice of the present invention are opiate receptor agonists or antagonists and generally are compounds corresponding to Formula (24)

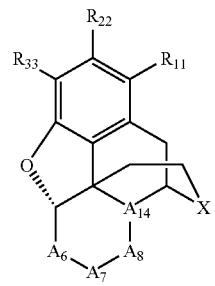

(24)

wherein -$A_6$-$A_7$-$A_8$-$A_{14}$- corresponds to Formulae (S), (T), (U), (V), (W), (X), (Y), or

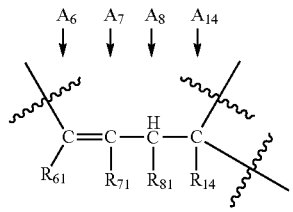

(S)

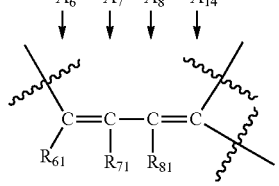

(T)

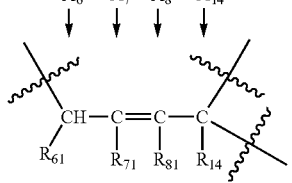

(U)

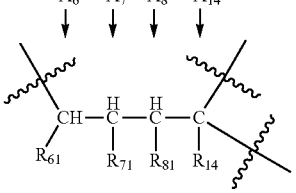

(V)

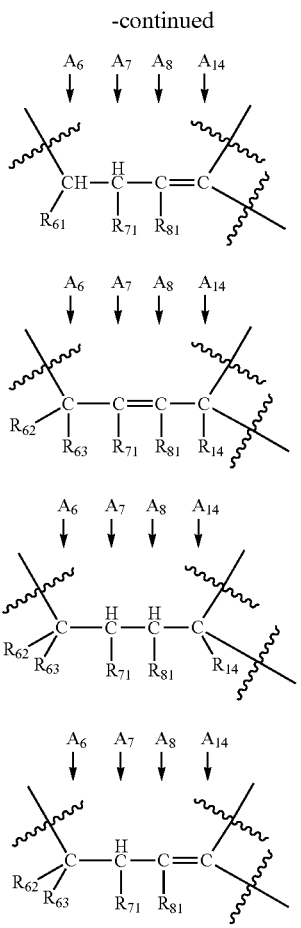

(Z):
$R_{11}$ and $R_{22}$ are independently hydrogen, substituted and unsubstituted acyl, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxy, protected hydroxy, or nitro;

$R_{14}$ is hydrogen, acyloxy, hydroxy, or protected hydroxy;

$R_{17}$ is hydrogen, alkyl, alkoxy, alkylenecycloalkyl, allyl, alkenyl, acyl, formyl, formyl ester, formamide, or benzyl;

$R_{17a}$ and $R_{17b}$ are independently hydrogen, alkyl, cycloalkyl, cycloalkylalkyl, aryl, or benzyl;

$R_{18}$ and $R_{19}$ are independently hydrogen, substituted and unsubstituted acyl, alkenyl, alkoxy, alkoxyaryl, alkyl, alkylamino, arylthio, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, halo, haloalkoxy, haloalkyl, heteroaryl, heterocyclic, hydroxyalkyl, hydroxy, or nitro, or $R_{18}$ and $R_{19}$ together form keto;

$R_{33}$ is alkoxy, acyloxy, hydroxy, or protected hydroxy;

$R_{61}$ is alkoxy, acyloxy, hydroxy, or protected hydroxy;

$R_{62}$ and $R_{63}$ are independently hydrogen, alkyl, alkenyl, alkynyl, allyl, alkoxy, alkylthio, acyloxy, or aryl, together form keto, or together with the carbon atom to which they are attached form a ketal, dithioketal, or monoketal;

$R_{71}$ and $R_{81}$ are independently hydrogen, hydrocarbyl, substituted hydrocarbyl, or halo; and X is oxygen, sulfur, —S(O)—, —S(O$_2$)—, —C(R$_{18}$)(R$_{19}$)—, —N(R$_{17}$)—, or —N(R$_{17a}$R$_{17b}$)—.

In a particular embodiment, the products and intermediates produced according to the present invention are useful in the preparation of a morphinan compound corresponding to Formula (24) wherein X is —N(R$_{17}$)— and R$_{17}$ is defined as above.

For purposes of clarity, the carbon atoms of Formulae (S), (T), (U), (V), (W), (X), (Y), and (Z) corresponding to $A_6$, $A_7$, $A_8$, and $A_{14}$ of Formula (24), respectively, have been identified (by indicating with an arrow which carbon atom corresponds to each). Further, squiggly lines have been included in Formulae (S), (T), (U), (V), (W), (X), (Y), and (Z) to indicate the points of attachment to the polycyclic ring of Formula (24).

Exemplary morphinans that may be produced according to a variety of methods include, for instance, nordihydrocodeinone (i.e., Formula (24) wherein $R_{11}$, $R_{17}$, and $R_{22}$ are hydrogen, $R_{33}$ is methoxy, X is —N(R$_{17}$)—, and -$A_6$-$A_7$-$A_8$-$A_{14}$- corresponds to Formula (Y) wherein $R_{14}$ is hydrogen, $R_{62}$ and $R_{63}$ together form keto, and $R_{71}$ and $R_{81}$ are hydrogen) (which corresponds to Formula (241) below); dihydrocodeinone (i.e., Formula (24) wherein $R_{11}$ and $R_{22}$ are hydrogen, $R_{17}$ is methyl, $R_{33}$ is methoxy, X is —N(R$_{17}$)—, and -$A_6$-$A_7$-$A_8$-$A_{14}$- corresponds to Formula (Y) wherein $R_{14}$ is hydrogen, $R_{62}$ and $R_{63}$ together form keto, and $R_{71}$ and $R_{81}$ are hydrogen) (which corresponds to Formula (242) below); noroxymorphone (i.e., Formula (24) wherein $R_{11}$, $R_{17}$, and $R_{22}$ are hydrogen, $R_{33}$ is hydroxy, X is —N(R$_{17}$)—, and -$A_6$-$A_7$-$A8$-$A_{14}$- corresponds to Formula (Y) wherein $R_{14}$ is hydroxy, $R_{62}$ and $R_{63}$ together form keto, and $R_{71}$ and $R_{81}$ are hydrogen) (which corresponds to Formula (243) below); and salts, intermediates, and analogs thereof.

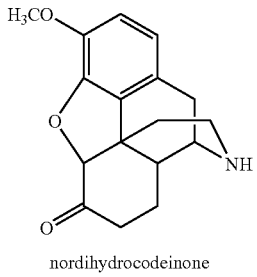

nordihydrocodeinone (241)

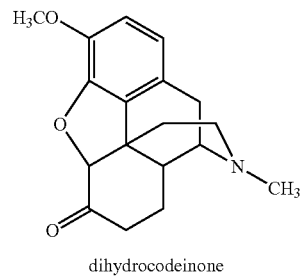

dihydrocodeinone (242)

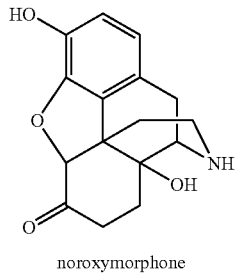

noroxymorphone (243)

Definitions

The term "acyl," as used herein alone or as part of another group, denotes the moiety formed by removal of the hydroxyl group from the group COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, substituted hydrocarbyl, or heterocyclo, and $R_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

Having described the invention in detail, it will be apparent that modifications and variations are possible without departing from the scope of the invention defined in the appended claims.

EXAMPLES

The following non-limiting examples are provided to further illustrate the present invention.

Example 1

Preparation of Compound 711 from Compound 611 and Compound 712 from Compound 612

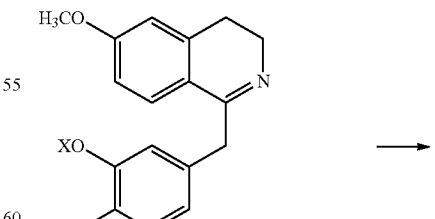

Compound 610 (X = Na)
Compound 611 (X = H)
Chemical Formula: $C_{18}H_{19}NO_3$
Exact Mass: 297.1
Molecular Weight: 297.3

-continued

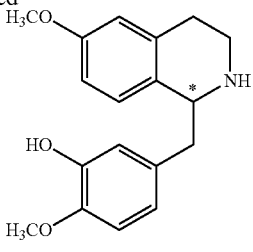

Compound 711
Chemical Formula: C₁₉H₂₃NO₅
Exact Mass: 345.2
Molecular Weight: 345.4

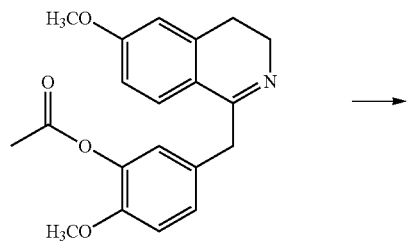

Compound 612
Chemical Formula: C₂₀H₂₁NO₄
Exact Mass: 339.1
Molecular Weight: 339.4

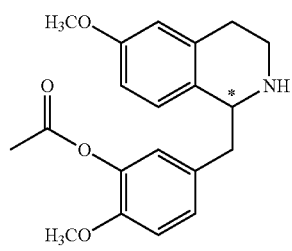

Compound 712
Chemical Formula: C₂₁H₂₅NO₆
Exact Mass: 387.2
Molecular Weight: 387.4

To a 5 L dried reactor under inert atmosphere, was added acetonitrile (1.4 L, anhydrous). To the acetonitrile, triethylamine (455.8 g, 4.5 moles) was introduced. The reaction flask was chilled to 5° C. 98% Formic acid (548.1, 8.75 moles) was added dropwise while maintaining the temperature below 30° C. After the formic acid was added, the formed salt solution was degassed for 1 hour. Compound 610 (434.5, 1.36 moles) was added all at once followed by 3.0 g dichloro (p-cymene)ruthenium (II) dimer and 3.0 g of (1S,2S)-(+)-N-4-toluenesulfonyl)-1,2-diphenylethylene-1,2-diamine.

When Compound 610 was used as the starting material, an additional 1.0 equivalent of 98% formic acid was added to convert the Na salt to the phenol in situ. The reaction initially turned green, then slowly changed to yellow. The reaction mixture was stirred for 16 hours at room temperature. HPLC indicated the reaction was complete. The product, Compound 711 (460 g, 97.9% yield, 97.3% assay, 99% e.e.(R)), was isolated by filtering the solid and washing it with acetonitrile (500 mL) followed by drying overnight (40° C., 30 in Hg). Typically, the yields of this reaction were 95% and the enantiomeric excess was 95% R. When (1R,2R)-(−)-N-4-toluenesulfonyl)-1,2-diphenylethylene-1,2-diamine was substituted for (1S,2S)-(+)-N-4-toluenesulfonyl)-1,2-diphenylethylene-1,2-diamine in this process the S-enantiomer of Compound 711 was produced.

To produce Compound 711 in high enantiomeric purity, a general ratio of the reactants must be maintained. For example, a ratio of about 2 equivalents of triethylamine to 5 equivalents of formic acid is desired. Thus, generally, a ratio of about 3.2 to 3.3 equivalents of triethylamine to 7.8 to 7.9 equivalents of 98% formic acid was used. Typically, about 0.5 wt % to 1.5 wt % of Ru catalyst and chiral ligand was used. The reaction time directly depends on the catalyst and ligand loading; for example, lower catalyst and ligand loading results in a longer reaction time.

Example 2

Preparation of Compound 811 from Compound 711

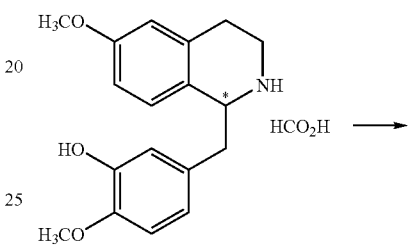

Compound 711
Chemical Formula: C₁₉H₂₃NO₅
Exact Mass: 345.2
Molecular Weight: 345.4

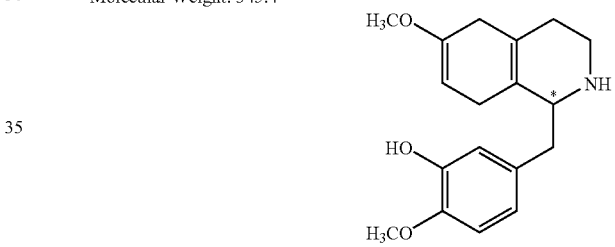

Compound 811
Chemical Formula: C₁₈H₂₃NO₃
Exact Mass: 301.2
Molecular Weight: 301.4

To a 5 L dried reaction flask was added Compound 711 (392.5 g, 1.14 moles), isopropyl alcohol (500 mL, anhydrous), and tetrahydrofuran (1.0 L, anhydrous, inhibitor free). The obtained slurry was cooled to −60° C. Anhydrous ammonia (approximately 1.5 L) was condensed into the slurry. The mixture was stirred for 30 minutes while maintaining the temperature at −60° C. Then, lithium metal (30.2 g, 4.35 moles) was added to the reaction mixture in 5 portions over an hour period. After the last addition, the color of the reaction was blue. HPLC analysis indicated the reaction was complete. Then, anhydrous methanol (400 mL) was added dropwise. After the addition was complete, the reaction mixture was slowly warmed to room temperature (approximately 8 hours with good stirring) allowing excess ammonia to evaporate. Distilled water (750 mL) was added to the mixture. After stirring for 30 minutes, glacial acetic acid was added slowly to a pH of 9.5 to 10. After stirring for 1 hour, the product, Compound 811 (330.1 g, 96% yield, 98.6% e.e. (R)), was isolated by filtration after washing the solid with distilled water (1.0 L) and drying under vacuum (30 C, 30 in Hg, 48 hours).

Generally, the solvent ratio of isopropyl alcohol (IPA) to tetrahydrofuran (THF-anhydrous) to liquid ammonia is about 1 to 2 to 3. Depending on the activity of the lithium metal about 1 to 30 equivalents are used. The lithium metal was added until electron transfer (blue color) was observed.

Example 3

Preparation of Compound 711 from Compound 611

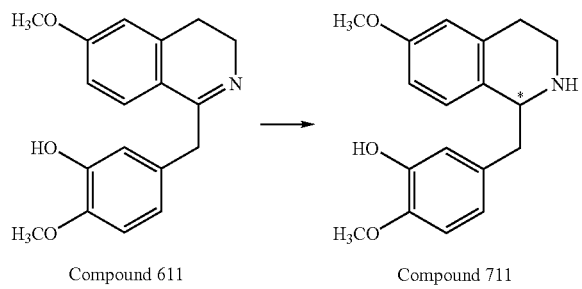

Compound 611      Compound 711

Triethylamine (1.06 g per gram of Compound 611) and acetonitrile (6 mL per gram of Compound 611) were added to a reactor equipped with a mechanical stirrer. Formic acid (1.2 g per gram of Compound 611) was added in four portions to the reactor resulting in an exotherm. The reaction temperature was controlled below 80° C. during the addition. After cooling to room temperature, a solution of 5 equivalents formic acid to 2 equivalents triethylamine in acetonitrile was formed. Compound 611 was added to form a suspension. It was flushed with nitrogen for 15 min and the Ru catalyst 111 described below (0.01 g per gram of Compound 611) was added. The suspension was again flushed with nitrogen for 15 minutes and stirred at room temperature for 10 hours. The end point of the reaction was determined by HPLC (Compounds 711:611 were >99:1). The mixture was diluted with water (9 mL per gram of Compound 611) until dissolved. To the solution, 28% ammonium hydroxide (1.0 mL per gram of Compound 611) was added to give a precipitate. The pH of the mixture was further adjusted with ammonium hydroxide (28%) to about 9.3-9.7. The resulting suspension was filtered and the solid obtained was washed with water (3×1.0 mL per gram of Compound 611) and dried under vacuum (20 inches) and flowing nitrogen at 60° C. for 20 hours to give the product as an off-white solid. Yields ranged from 80% to 95% and R:S ratio was 95:5 (90% e.e.).

Example 4

Preparation of Compound 711 from Compound 611

Table 1 shows that the results for the catalytic asymmetric reduction of Compound 611 to Compound 711. The reaction was carried out in either acetonitrile ($CH_3CN$) or methylene chloride ($CH_2Cl_2$) at room temperature using from 0.5 mol % to 2 mol % catalyst loading. Excess formic acid-triethylamine (5:2) was used as the reducing reagent. The catalyst was prepared by combining equal amounts of (1S,2S)-(+)-N-4-toluenesulfonyl)-1,2-diphenylethylene-1,2-diamine and either dichloro(p-cymene) ruthenium (II) dimer (catalyst 111), dichloro(benzene)ruthenium (II) dimer (catalyst 112), or dichloro(mesitylene)ruthenium (II) dimer (catalyst 114). The yields and enantioselectivity resulting from the asymmetric reduction are listed in table 1.

TABLE 1

Asymmetric reduction of imine Compound 611 to amine Compound 711.

| Catalyst | Solvent | Catalyst:substrate | reaction time (h) | Yield (%) | Ratio of R:S |
|---|---|---|---|---|---|
| 112 | $CH_3CN$ | 1:100 | 16 | 47 | 90:10 |
| 112 | $CH_2Cl_2$ | 1:100 | 16 | 89 | 89:11 |
| 111 | $CH_2Cl_2$ | 1:100 | 16 | 88 | 96:4 |
| 111 | $CH_3CN$ | 1:100 | 16 | 94 | 100:0 |
| 111 | $CH_2Cl_2$ | 1:200 | 16 | 92 | 100.0:0 |
| 111 | $CH_2Cl_2$ | 1:50 | 16 | 94 | 98.5:1.5 |
| 114 | $CH_2Cl_2$ | 1:100 | 16 | 92 | 48.5:51.5 |

Example 5

Preparation of Compound 711 from Compound 613

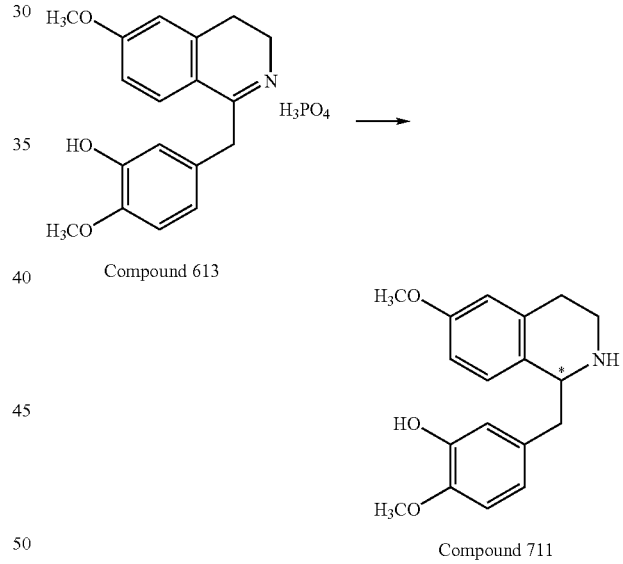

Compound 613

Compound 711

The results in Table 2 show that Compound 613 (the salt of Compound 611) can be directly reduced to Compound 711 using the reaction conditions of Table 1 with excess base. The reactions of Table 2 were carried out in acetonitrile with Compound 611 (1.68 mmol), 5:2 formic acid-triethylamine (10.8 mmol), and 1 mol % Ru catalyst 111.

TABLE 2

Asymmetric reduction of Compound 613

| $H_3PO_4$ mmol | NaOAc mmol | $NaHCO_3$ mmol | $NEt_3$ mmol | NaCl mmol | time (h) | conversion 611/613/711R/711S | 711R/711S |
|---|---|---|---|---|---|---|---|
| 3.36 | | | | | 15 | 62/11/19/3 | |
| 6.72 | | | | | 15 | 78/19/3/0 | |

TABLE 2-continued

Asymmetric reduction of Compound 613

| H$_3$PO$_4$ mmol | NaOAc mmol | NaHCO$_3$ mmol | NEt$_3$ mmol | NaCl mmol | time (h) | conversion 611/613/711R/711S | 711R/711S |
|---|---|---|---|---|---|---|---|
| 13.4 | | | | | 15 | 83/15/1/0 | |
| 6.72 | | | | | 65 | 86/11/2/0 | |
| 6.72 | | | 6.72 | | 65 | 2/5/85/3 | 97/3 |
| 6.72 | | | 13.4 | | 65 | 1/3/93/3 | 97/3 |
| | | | | | 65 | 1/2/93/3 | 97/3 |
| 6.72 | | 6.72 | | 6.72 | 15 | 26/2/61/9 | 87/13 |
| 6.72 | 6.72 | | | 6.72 | 15 | 66/6/19/6 | 75/25 |
| 6.72 | 6.72 | | | | 38 | 1/2/86/7 | 92/8 |
| 6.72 | 13.4 | | | | 38 | 0.1/1.6/88/6 | 93/67 |
| | | | 6.72 | | 15 | 0.6/3/92/3 | 97/3 |
| | | | 13.4 | | 15 | 0.6/3/92/3 | 97/3 |

Example 6

Preparation of Compound 713 from Compound 611

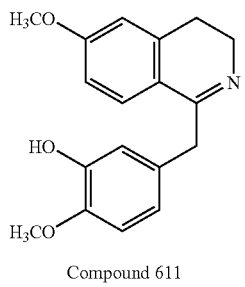

Compound 611

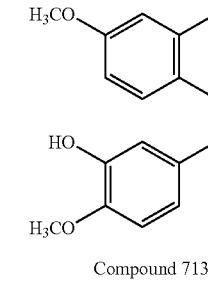

Compound 713

Triethylamine (1.06 g per gram of Compound 611) and acetonitrile (6 mL per gram of Compound 611) were added to a reactor equipped with mechanical stirrer. Formic acid (1.2 g per gram of Compound 611) was added in four portions to the reactor. The exothermic reaction temperature was controlled at below 80° C. during the addition of formic acid. The reaction mixture was cooled to room temperature to form a solution of formic acid-triethylamine (5:2) in acetonitrile. Compound 611 was added to the solution to form a suspension. After flushing with nitrogen for 15 minutes, the Ru catalyst 111 (0.01 g per gram of Compound 611) was added. The suspension was again flushed with nitrogen for 15 minutes and stirred at room temperature for 10 hours. The reaction mixture was heated to 100° C. for 2 hours to form Compound 713; Compound 713 has a formyl group attached to the nitrogen. Compound 713 was isolated as a solid by pouring the solution into an ice cold ammonium hydroxide solution (20 mL per gram of Compound 611).

Example 7

Preparation of Compound 811 from Compound 711

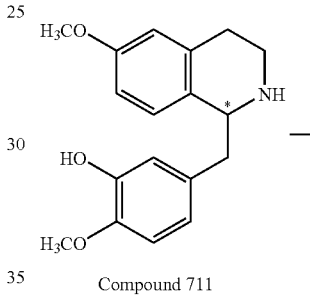

Compound 711

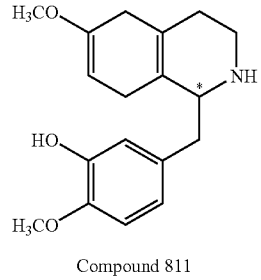

Compound 811

To a reactor, isopropyl alcohol (IPA) (2.0 mL/g of Compound 711), tetrahydrofuran (THF) (4.0 mL/g of Compound 711) and the Compound 711 (pre-dried to the limit of detection (LOD) or <0.2% water) were added. The suspension was cooled to −55° C. with stirring in a dry-ice bath. Liquid ammonia (10 mL/g of Compound 711) was condensed into the reactor at −55° C. The reaction mixture was cooled at −55° C. and was flushed with nitrogen for 15 minuntes. Sodium t-butoxide (NaOt-Bu) (0.35 g/g of Compound 711) was added and stirred for another 15 minutes. Lithium (cut, 0.070 g/g of Compound 711) was added in three portions to the mixture (⅓×0.070 g/g of Compound 711 in each portion) and the temperature of the reaction mixture was maintained at −45 to −55° C. by using a dry-ice bath and by controlling the addition rate. The reaction mixture was stirred for 50 minutes until all of the lithium was added. If the blue color of the reaction mixture lasted for more than 30 minutes the reaction was complete; otherwise, more lithium was added until the blue color persisted for 30 minutes. Methanol (1.0 g/g of Compound 711) was added after the reaction was determined to be complete. The reaction mixture was warmed from −28° C. to 20° C. to remove most of the ammonia and then stirred for another 1 hour after the temperature reached 20° C. Water was degassed by bubbling nitrogen through it for 20 minutes and this degassed water (10 mL/g of Compound 711) was added under nitrogen to the above mixture. The suspension was stirred for 30 minutes (pH=12.4) to form a solution. A solution of aqueous acetic acid (acetic acid at 0.95 ml/g of Compound 711 and H₂O at 1.90 mL/g of Compound 711) was added to form a suspension (pH=7.8). The suspension's pH was adjusted to 8.8 to 9.2 with 28% ammonium hydroxide (~0.25 mL/g of Compound 711). The suspension was stirred for 1 hour and filtered. The reactor was repeatedly rinsed with water (3.0 mL/g of Compound 711) which was then used to wash the solid filtrate. The solid was further washed with water (3.0 mL/g of Compound 711) and dried under flowing air for 4 h and then dried under vacuum (20 inches) at 60° C. for 20 hours to give the product as an off-white solid in about 90% yield.

Example 8

Preparation of Compound 811 and 815 from Compound 711

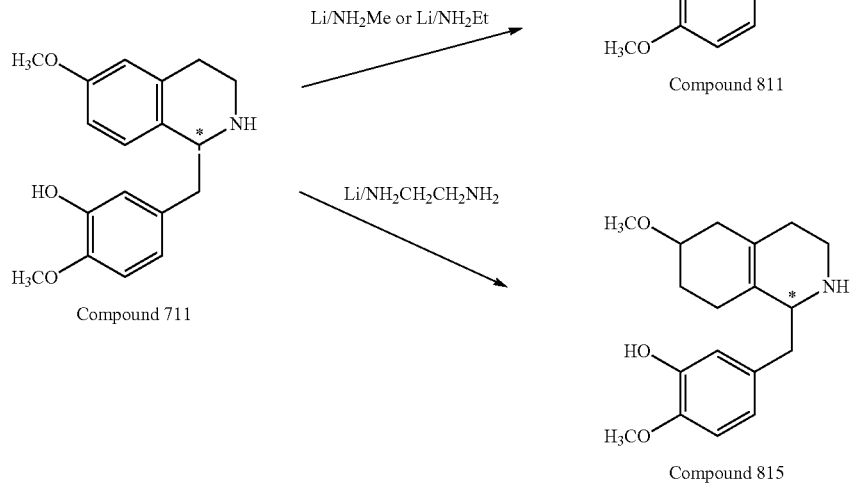

In order to carry out the Birch reduction at higher temperature, the low boiling point reagent, ammonia, was replaced with higher boiling point reagents; for example, methylamine, ethylamine, or ethylenediamine. It was found that both methylamine and ethylamine could be used as electron transfer reagents to give the desired product at −10° C. to 10° C. When Li/NH₂Me/THF/t-BuOH was used for the reduction of Compound 711, 80% yield of Compound 811 was obtained as a solid. When Li/NH₂Et/THF/t-BuOH was used for the reduction of Compound 711, Compound 811 was formed in 50% to 70% yield. The reaction of Compound 711 in the system of Li/NH₂CH₂CH₂NH₂/THF under reflux formed undesired Compound 815.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A process for the preparation of a 1,2,3,4-tetrahydroisoquinoline corresponding to Formula 700, the process comprising treating a 3,4-dihydroisoquinoline corresponding to Formula 600 with an asymmetric catalyst in the presence of silver tetrafluoroborate, and a hydrogen source

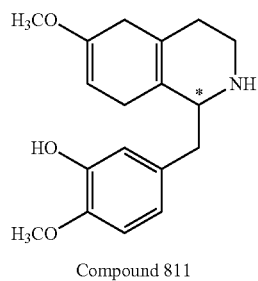

Compound 811

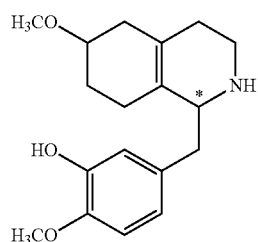

Compound 815

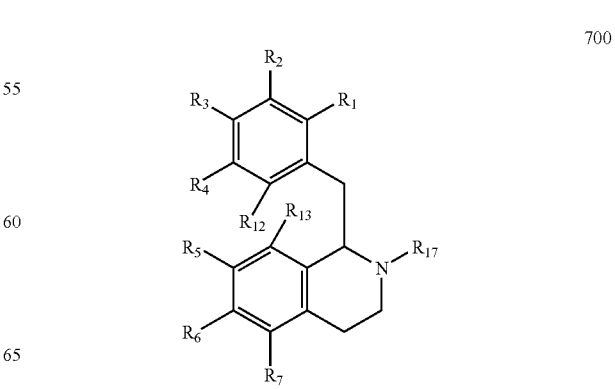

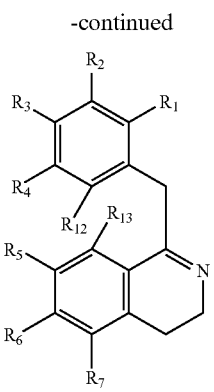

wherein
- $R_1$ and $R_7$ are independently hydrogen, hydrocarbyl, substituted hydrocarbyl, or —$OR_{111}$;
- $R_2$ is hydrogen, hydrocarbyl, substituted hydrocarbyl, halo, or —$OR_{211}$;
- $R_3$ is hydrogen, hydrocarbyl, substituted hydrocarbyl, or —$OR_{311}$;
- $R_4$ is hydrogen, hydrocarbyl, substituted hydrocarbyl, halo, or —$OR_{411}$;
- $R_5$ and $R_6$ are independently hydrogen, hydrocarbyl, substituted hydrocarbyl, or —$OR_{511}$;
- $R_{12}$ is hydrogen, hydrocarbyl, substituted hydrocarbyl, halo, or —$OR_{121}$;
- $R_{13}$ is hydrogen, hydrocarbyl, substituted hydrocarbyl, halo, or —$OR_{511}$;
- $R_{17}$ is hydrogen, or acyl;
- $R_{111}$ is hydrogen, hydrocarbyl, or substituted hydrocarbyl;
- $R_{211}$ is hydrogen, hydrocarbyl, —(O)$R_{212}$, —(O)NH$R_{213}$, or —SO$_2R_{214}$, $R_{212}$, $R_{213}$, and $R_{214}$ are independently hydrocarbyl or substituted hydrocarbyl;
- $R_{311}$ is hydrogen, hydrocarbyl, —(O)$R_{312}$, —(O)NH$R_{313}$, or —SO$_2R_{314}$, $R_{312}$, $R_{313}$, and $R_{314}$ are independently hydrocarbyl or substituted hydrocarbyl;
- $R_{411}$ is hydrogen, hydrocarbyl, —(O)$R_{412}$, —(O)NH$R_{413}$, or —SO$_2R_{414}$, $R_{412}$, $R_{413}$, and $R_{414}$ are independently hydrocarbyl or substituted hydrocarbyl;
- $R_{511}$ is hydrogen, hydrocarbyl, or substituted hydrocarbyl; and
- $R_{121}$ is hydrogen, hydrocarbyl, or substituted hydrocarbyl.

2. The process of claim 1, wherein:
- $R_2$ is —$OR_{211}$;
- $R_{211}$ is hydrogen, alkyl, —C(O)$R_{212}$, —C(O)NH$R_{213}$, or SO$_2R_{214}$; and
- $R_{212}$, $R_{213}$, and $R_{214}$ are independently alkyl or aryl.

3. The process of claim 1, wherein:
- $R_3$ is —$OR_{311}$;
- $R_{311}$ is hydrogen, alkyl, —C(O)$R_{312}$, —C(O)NH$R_{313}$, or —SO$_2R_{314}$; and
- $R_{312}$, $R_{313}$, and $R_{314}$ are independently alkyl or aryl.

4. The process of claim 1, wherein:
- $R_4$ is —$OR_{411}$;
- $R_{411}$ is hydrogen, alkyl, —C(O)$R_{412}$, —C(O)NH$R_{413}$, or —SO$_2R_{414}$; and
- $R_{412}$, $R_{413}$, and $R_{414}$ are independently alkyl or aryl.

5. The process of claim 1, wherein $R_{12}$ is alkyl, allyl, benzyl, or halo.

6. The process of claim 1, wherein $R_{212}$, $R_{213}$, $R_{214}$, $R_{312}$, $R_{313}$, $R_{314}$, $R_{412}$, $R_{413}$, and $R_{414}$ are methyl.

7. The process of claim 1, wherein $R_3$ is methoxy, R4 is hydroxyl, —OC(O)CH$_3$, —OC(O)Ph, or —OSO$_2$CH$_3$, $R_6$ is methoxy, and $R_1$, $R_2$, $R_5$, $R_7$, $R_{12}$, and $R_{13}$ are hydrogen.

8. The process of claim 1, wherein:
- $R_2$ is —$OR_{211}$;
- $R_{211}$ is hydrogen, alkyl, —C(O)$R_{212}$, —(O)NH$R_{213}$, or —SO$_2R_{214}$;
- $R_{212}$, $R_{213}$, and $R_{214}$ are independently alkyl or aryl;
- $R_3$ is —$OR_{311}$;
- $R_{311}$ is hydrogen, alkyl, —C(O)$R_{312}$, —(O)NH$R_{313}$, or —SO$_2R_{314}$;
- $R_{312}$, $R_{313}$, and $R_{314}$ are independently alkyl or aryl;
- $R_4$ is —$OR_{411}$;
- $R_{411}$ is hydrogen, alkyl, —C(O)$R_{412}$, —(O)NH$R_{413}$, or —SO$_2R_{414}$; and
- $R_{412}$, $R_{413}$, and $R_{414}$ are independently alkyl or aryl.

9. The process of claim 8, wherein $R_{212}$, $R_{213}$, $R_{214}$, $R_{312}$, $R_{313}$, $R_{314}$, $R_{412}$, $R_{413}$, and $R_{414}$ are methyl; $R_3$ is methoxy, $R_4$ is hydroxyl, —OC(O)CH$_3$, —OC(O)Ph, or —OSO$_2$CH$_3$, $R_6$ is methoxy, and $R_1$, $R_2$, $R_5$, $R_7$, $R_{12}$, and $R_{13}$ are hydrogen.

10. The process of claim 1, wherein about 0.005 g to about 0.015 g of silver tetrafluoroborate per equivalent of 3,4-dihydroisoquinoline is used.

11. The process of claim 1, wherein the temperature of the reaction mixture is from about 20° C. to about 30° C.

12. The process of claim 1, wherein the asymmetric catalyst comprises a metal or a metal source and a chiral ligand.

13. The process of claim 12, wherein the metal or metal source is chosen from ruthenium, a ruthenium complex, osmium, an osmium complex, rhodium, a rhodium complex, iridium, iridium complex, and combinations thereof.

14. The process of claim 12, wherein the chiral ligand has the structure of formulae 670 or 680

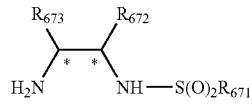

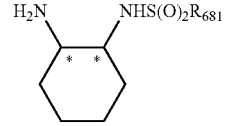

wherein
- $R_{671}$, $R_{672}$, and $R_{673}$ are independently alkyl or aryl;
- $R_{681}$ is alkyl or aryl.

15. The process of claim 12, wherein the chiral ligand is (1S,2S)-(+)-N-4-tolylsulfonyl-1,2-diphenylethylene-1,2-diamine.

16. The process of claim 1, wherein the hydrogen source is a formic acid-triethylamine salt mixture.

17. The process of claim 16, wherein the ratio of formic acid to triethylamine is 5 to 2.

* * * * *